United States Patent
Batarseh et al.

(10) Patent No.: US 7,147,064 B2
(45) Date of Patent: Dec. 12, 2006

(54) LASER SPECTROSCOPY/CHROMATOGRAPHY DRILL BIT AND METHODS

(75) Inventors: Samih Batarseh, Mount Prospect, IL (US); Kent Perry, Schaumburg, IL (US); Brian C. Gahan, Cary, IL (US)

(73) Assignee: Gas Technology Institute, Des Plaines, IL (US)

( * ) Notice: Subject to any disclaimer, the term of this patent is extended or adjusted under 35 U.S.C. 154(b) by 224 days.

(21) Appl. No.: 10/843,535

(22) Filed: May 11, 2004

(65) Prior Publication Data

US 2005/0269132 A1    Dec. 8, 2005

(51) Int. Cl.
 *E21B 7/15* (2006.01)
(52) U.S. Cl. .............................. 175/11; 175/16; 175/40; 299/14
(58) Field of Classification Search .................. 175/11, 175/16, 40, 50; 299/14
See application file for complete search history.

(56) References Cited

U.S. PATENT DOCUMENTS

| 3,871,485 | A | | 3/1975 | Keenan, Jr. |
| 4,066,138 | A | | 1/1978 | Salisbury et al. |
| 4,090,572 | A | | 5/1978 | Welch |
| 4,113,036 | A | * | 9/1978 | Stout ............................ 175/11 |
| 4,199,034 | A | * | 4/1980 | Salisbury et al. ............. 175/11 |
| 5,107,936 | A | | 4/1992 | Foppe |
| 6,206,108 | B1 | * | 3/2001 | MacDonald et al. ........... 175/24 |
| 6,281,489 | B1 | | 8/2001 | Tubel et al. |
| 6,863,136 | B1 | * | 3/2005 | Bar-Cohen et al. ........... 175/55 |
| 6,880,646 | B1 | * | 4/2005 | Batarseh ....................... 175/15 |
| 6,888,097 | B1 | * | 5/2005 | Batarseh .................. 219/121.7 |
| 2002/0134587 | A1 | * | 9/2002 | Rester et al. ................. 175/48 |
| 2003/0000741 | A1 | * | 1/2003 | Rosa ............................ 175/65 |

FOREIGN PATENT DOCUMENTS

JP        05118185 A  *  5/1993

* cited by examiner

*Primary Examiner*—David Bagnell
*Assistant Examiner*—Giovanna M. Collins
(74) *Attorney, Agent, or Firm*—Mark E. Fejer

(57) ABSTRACT

A drilling apparatus for well-boring having a drill bit assembly which includes a laser cutting assembly and a vacuum assembly. The vacuum assembly is adapted to intake vapors generated by the laser cutting assembly proximate the drill bit assembly during operation of the drilling apparatus. The collected vapors may then be processed by a chromatographic analyzer to determine the characteristics of the rock formation being drilled.

9 Claims, 4 Drawing Sheets

LASER SPECTROSCOPY/CHROMATOGRAPHY DRILL BIT AND METHODS

BACKGROUND OF THE INVENTION

1. Field of the Invention

This invention relates to a well-boring apparatus for drilling of subterranean formations for the recovery of fossil fuel deposits in the form of gas, oil and other liquified products. More particularly, this invention relates to an apparatus for drilling oil and gas wells comprising a hybrid drill bit, which provides both a cutting function and a separate heating function. The cutting function is provided by conventional cutting elements while the heating function is provided by a laser source that projects at least one laser beam ahead of the drill bit during the well-boring process to soften and/or melt materials, such as rock formations, disposed in the drilling path. This invention also relates to a well-boring apparatus comprising a drill bit assembly comprising at least one of a chromatographic analysis system and a laser spectroscopy assembly, whereby analysis of materials (e.g. rocks and vapors) disposed in the vicinity of the drill bit during operation of the drilling apparatus is enabled.

2. Description of Related Art

It is well known that substantial, heretofore untapped reserves of fossil fuels, including oil and natural gas, are buried deep within the ground. Access to these reserves may be obtained by means of well-bores that are produced by drilling apparatuses, which generally employ drill bits having hard and durable cutting contact elements. However, frequently these reserves are disposed beneath hard geological formations, e.g. rocks, which may even be impenetrable using conventional drilling equipment. Drilling of such hard formations requires a substantial amount of time and generally results in high costs. In addition, the drill bits used to drill through these hard formations are subject to extensive wear and/or damage. Impenetrable formations require the use of overly complex drilling routes in order to circumvent the formations and, in some cases, may result in complete abandonment of the drilling operation.

In addition to hard geological formations, unstable formations, e.g. shale, are frequently encountered, which formations may cause damage to and/or loss of drilling equipment. Unstable formations may also cause entrapment and subsequent abandonment of the drilling equipment.

One solution to the problems associated with the use of conventional drilling equipment, which as previously stated employ drill bits comprising one or more mechanical cutting elements, has been to use laser beams as a means of boring wells into the earth. For example, U.S. Pat. No. 4,066,138 to Salisbury et al. teaches an earth boring apparatus mounted above ground that directs an annulus of high powered laser energy downwardly for boring a cylindrical hole by fusing successive annular regions of the stratum to be penetrated at a power level that shatters and self-ejects successive cores from the hole. U.S. Pat. No. 4,113,036 to Stout teaches a laser drilling method and system of fossil fuel recovery in which a vertical bore hole is drilled into an underground formation, a laser beam is projected through the vertical borehole and reflected horizontally from the hole through the formation along a matrix of bores. U.S. Pat. No. 3,871,485 to Keenan, Jr. teaches a method of drilling using a laser beam in which a laser beam generator that is electrically connected to an inhole voltage generator actuated by drilling mud or other liquid passing through a laser beam housing connected to the drill string is positioned in the wellhole and a reflecting crystal is positioned within the laser beam housing to reflect the beam in an elliptical pattern across the formation to be penetrated. U.S. Pat. No. 4,090,572 to Welch teaches a method and apparatus for laser treatment of geological formations in which a laser beam is projected into a well bore along a beam guide so as to provide sufficient laser energy to melt or vaporize the formations under down-hole conditions. Similarly, U.S. Pat. No. 5,107,936 to Foppe teaches a heat drilling process employing laser beams as a heat source in which the profile of the borehole is melted down by the heat source and the resulting molten rock is pressed into the surrounding side rock during the drilling process such that only a gap defining the outer profile of the borehole is melted down, which surrounds a drill core, which is extracted at an adjustable distance behind the melting zone.

Numerous techniques exist for monitoring wellbores during the production and completion of wellbores, monitoring reservoir conditions, estimating quantities of hydrocarbons, operating downhole devices in wellbores, and determining the physical condition of the wellbore and downhole devices. Sensors disposed in the wellbore, such as temperature sensors, pressure sensors, accelerometers and hydrophones have been used to obtain continuous wellbore and formation information.

Conventional drilling of wells relies upon the use of a drilling fluid to recover shards of drilled rock and remove them from the well-bore, typically by bringing them up to the surface. These shards can then be filtered out of the mixture and analyzed to determine the type and properties of the rock formation being drilled. However, when lasers are used to perform drilling, the materials being drilled are vaporized, as a result of which there remain no shards of rock for analysis. It is, however, still important to be able to assess the conditions local to the drilling site.

SUMMARY OF THE INVENTION

It is one object of this invention to provide a drilling apparatus which is capable of drilling through geological formations that are impenetrable by conventional drill bits.

It is one object of this invention to provide a drilling apparatus which reduces the amount of wear and damage incurred by conventional drill bits when drilling through hard geological formations.

It is yet another object of this invention to provide a drilling apparatus for drilling through unstable geological formations, such as shale, which addresses issues of damage and equipment loss resulting from the use conventional drilling equipment when drilling through such formations.

It is yet a further object of this invention to provide a method and apparatus for determining conditions local to a drilling site, such as the type and properties of the rock formation being drilled.

These and other objects of this invention are addressed by a drilling apparatus for well-boring comprising a drill bit assembly comprising a laser cutting assembly and a vacuum assembly, where the vacuum assembly is adapted to intake vapors generated by the laser cutting assembly proximate the drill bit assembly during operation of the drilling apparatus. The vapors thus captured may readily be subjected to analysis. In accordance with one embodiment of this invention, the vapors are subjected to chromatographic analysis, which analysis may be performed either proximate to the drill bit assembly by a chromatographic analytic system disposed integral with or proximate to the drill bit assembly.

Alternatively, the captured vapors may be transported to a chromatographic analytic system disposed above ground for analysis. In accordance with another embodiment of this invention, the drill bit assembly comprises a laser spectroscopy assembly whereby spectroscopic analysis of the rock proximate to the drill bit assembly can be performed.

In accordance with one embodiment of this invention the drill bit assembly further comprises at least one mechanical cutting element suitable for cutting through rock. By virtue of this arrangement, in the event that the mechanical cutting elements are incapable of removing a particular rock formation, the laser cutting assembly can be employed independently to remove the rock by spalling, melting or vaporizing. In situations where unstable formation are encountered, the laser cutting assembly can be employed to melt these formations and displace them such that they will reset and reinforce the wellbore walls.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

As used herein, the term "downstream" refers to a direction towards the front of the drill bit assembly. As used herein, the term "upstream" refers to a direction towards the back of the drill bit assembly.

The invention disclosed herein is a drilling apparatus comprising a drill bit assembly that includes a laser drilling system, which may be of any design suitable for drilling through rock formations, coupled with one or more additional features. In accordance with one preferred embodiment of this invention, the drill bit assembly comprises at least one conventional mechanical cutting element, whereby the drill bit assembly is able to provide both a cutting function and a separate heating function. The cutting function is provided by the conventional cutting elements while the heating function is provided by the laser drilling system which comprises a laser source that projects at least one laser beam ahead of the conventional cutting elements during the well-boring process to soften and/or melt materials, such as rock formations disposed in the drilling path. In accordance with one embodiment of this invention, the drill bit assembly is coupled to a system providing chromatographic capabilities and/or spectroscopic capabilities.

Figure 1:
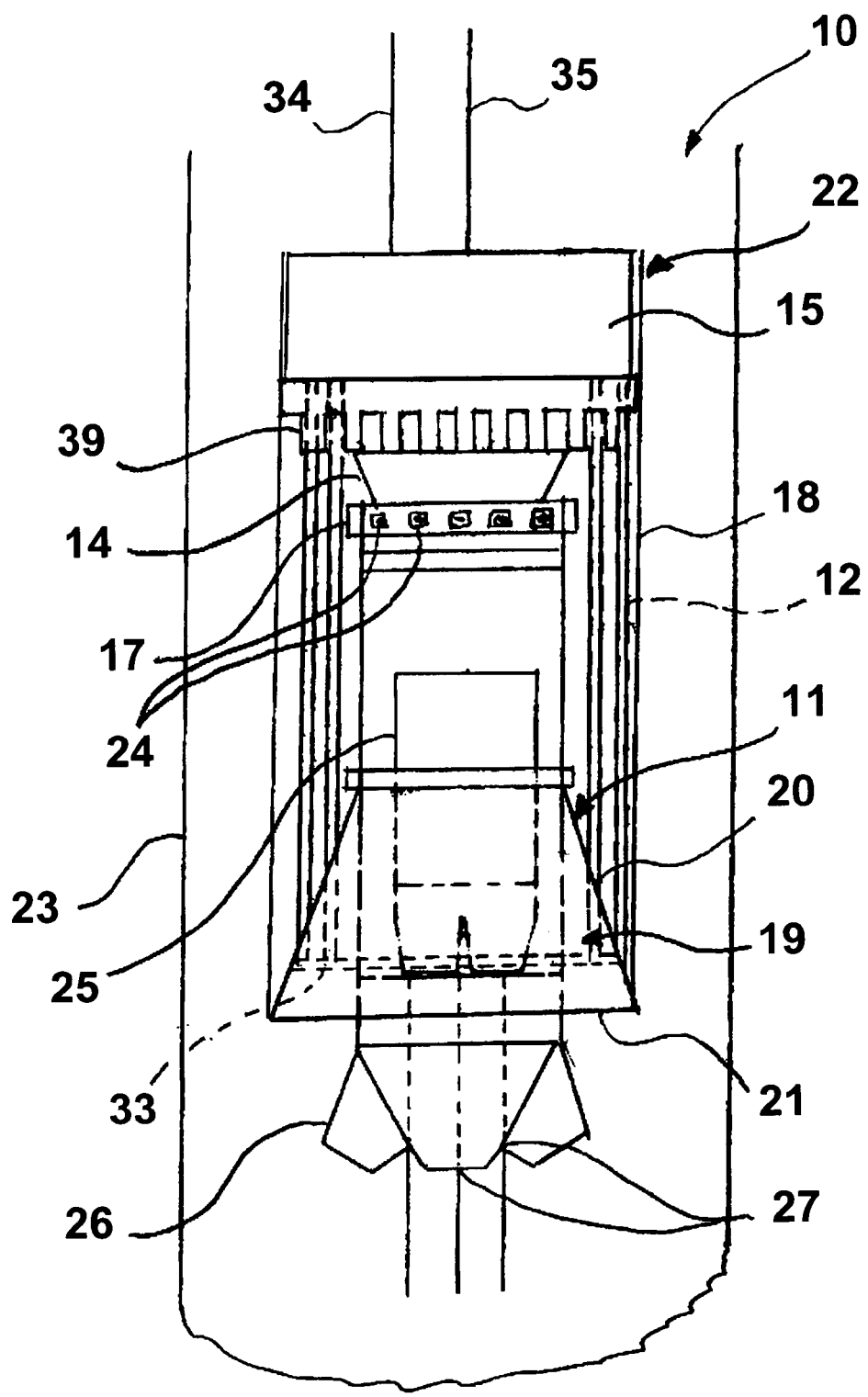
FIG. 1 is a schematic diagram showing a lateral view of a drilling apparatus in accordance with one embodiment of this invention.
Figure 2:
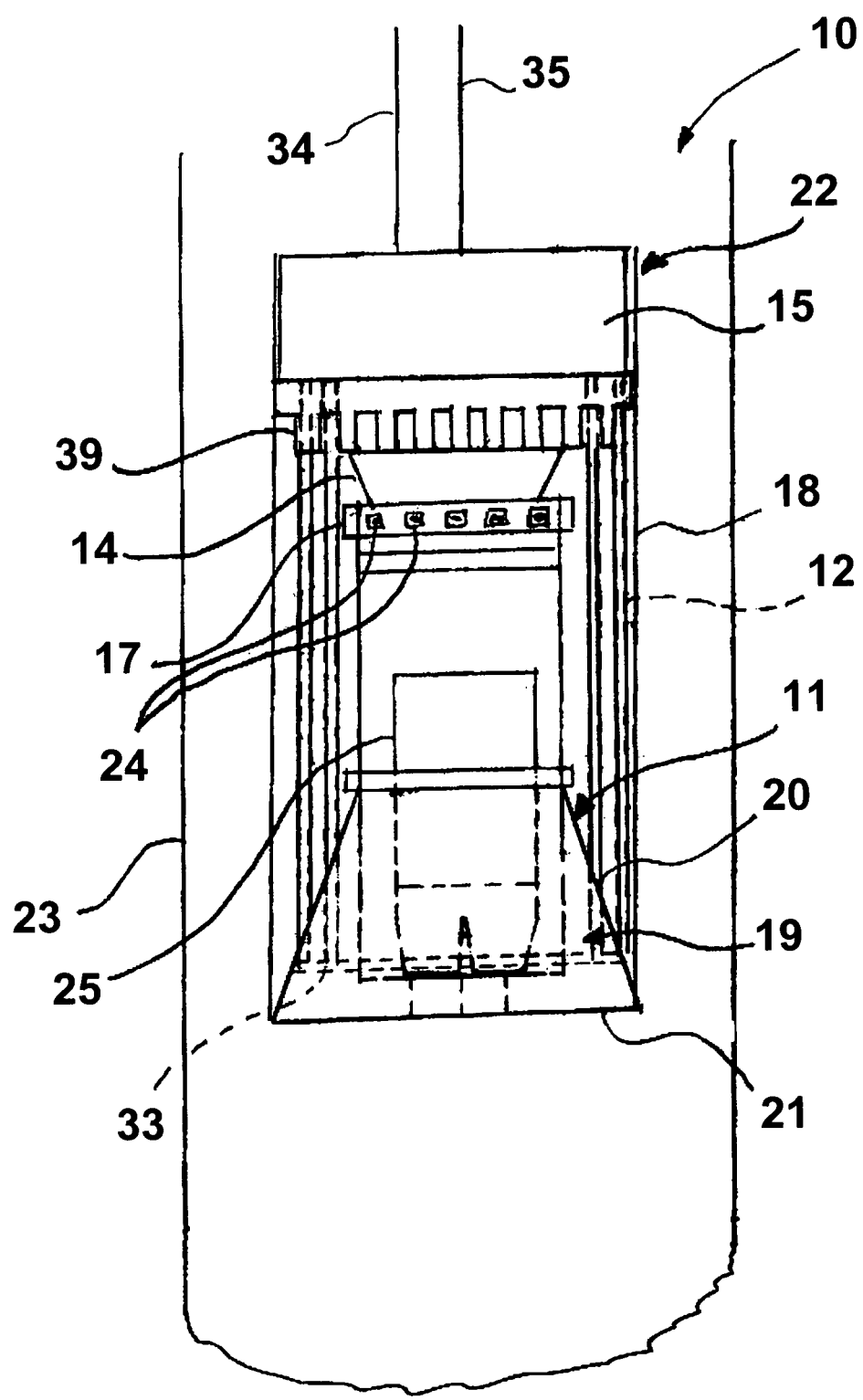
FIG. 2 is a schematic diagram of a lateral view of a drilling apparatus in accordance with another embodiment of this invention.
Figure 3:
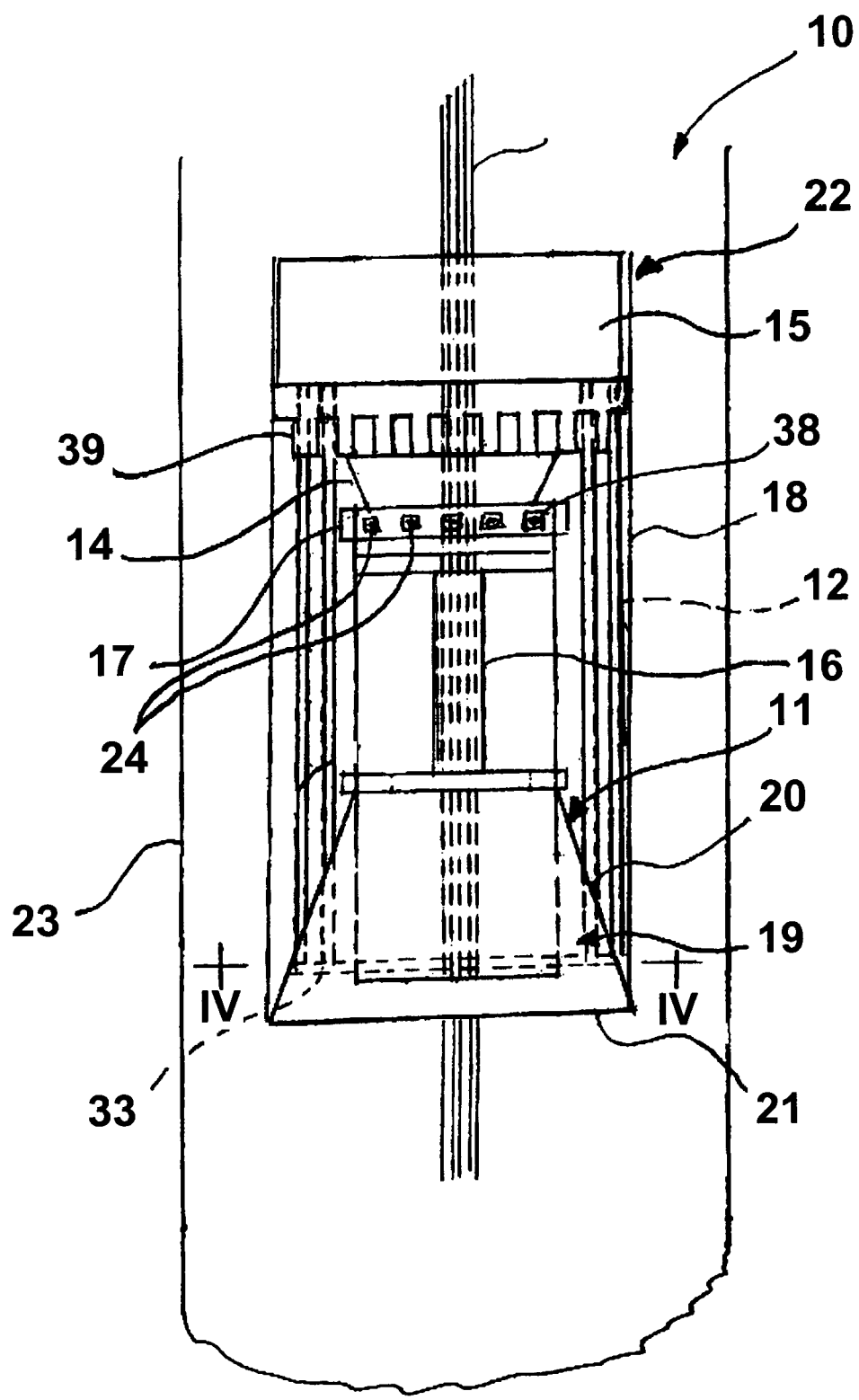
FIG. 3 is a schematic diagram of a lateral view of a drilling apparatus in accordance with one embodiment of this invention.

As shown in FIGS. 1, 2 and 3, drill bit assembly 10 having a downstream end 19 and an upstream end 22 is disposed at least partly within a protective enclosure 18, which is disposed in a wellbore 23. Power may be provided to drill bit assembly 10 by means of a power cable 35 connected between drill bit assembly 10 and a power source disposed above ground (not shown). Drill bit assembly 10 comprises a laser cutting assembly 11 proximate the downstream end 19 of drill bit assembly 10, which laser cutting assembly 11 comprises vacuum hood 20 having a vapor intake opening 21 whereby vapors generated during the drilling process may be collected for subsequent analysis. Total laser power, whether from a single beam or a plurality of beams, is preferably in the range of about 0.5 to about 15 kW, although more powerful lasers could be used. Suitable lasers may utilize continuous, chopped or pulsed waves. Disposed within vacuum hood 20 in accordance with one embodiment of this invention is a lens assembly 29 comprising a centrally disposed lens 30 (FIG. 4) for transmission of at least one laser beam to a location in front of drill bit assembly 10 during operation of the drilling apparatus, thereby enabling softening, melting or vaporization of the rock formations disposed in front of drill bit assembly 10. In accordance with one embodiment of this invention, conventional cutting elements 26 are disposed at the extreme downstream end of drill bit assembly 10, that is, downstream of laser cutting assembly 11. To enable transmission of lasers beams generated by laser cutting assembly 11, the cutting elements 26 form one or more laser beam path openings 27, thereby providing light transmission paths therethrough.

In accordance with one embodiment of this invention, laser cutting assembly 11 comprises a laser source 25 disposed within or proximate to drill bit assembly 10. Thus, as drill bit assembly 10 progresses down wellbore 23, laser source 25 progresses as well. In accordance with an alternative embodiment of this invention, the laser source is disposed above ground and light is transmitted by way of one or more fiber optic cables 37, as shown in FIG. 3, between the above-ground laser source and drill bit assembly 10. An advantage of this latter embodiment is that it obviates the need for providing control means for controlling the laser source down into the wellbore.

Figure 4:
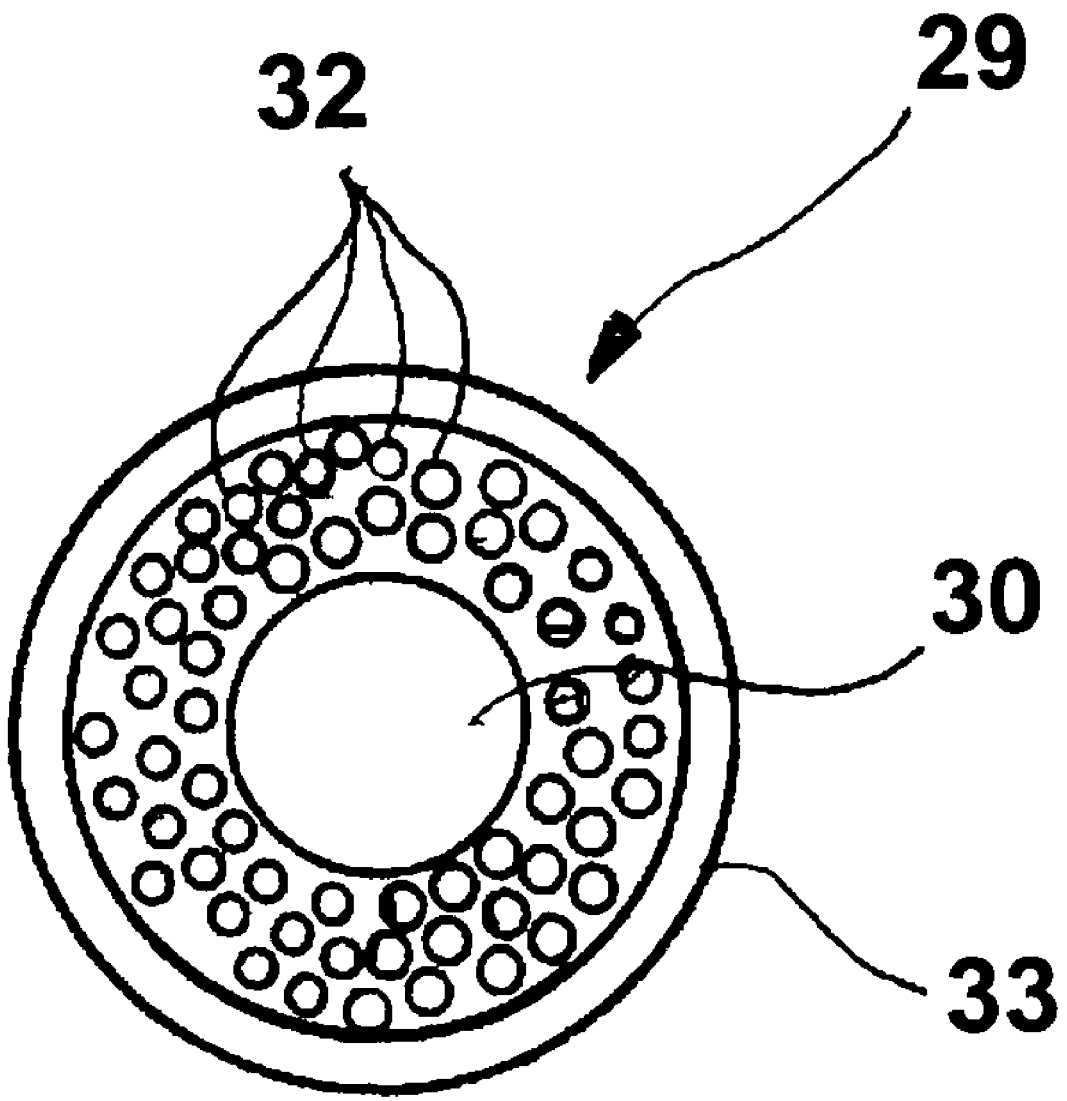
FIG. 4 is a view of the drilling apparatus shown in FIG. 3 taken along the line IV—IV.

As shown in FIG. 4, centrally disposed lens 30 is surrounded by a collar element 33 having a downstream facing face and an upstream facing face, the periphery of which is connected to an interior surface of vacuum hood 20. As shown in FIG. 4, collar element 33 forms a plurality of openings 32 to enable the transmission of vapors collected in vacuum hood 20 to an analytical system suitable for determining the properties of the rock formation being drilled. At least one vapor conduit 12 suitable for transmission of the vapors collected in vacuum hood 20 having a vapor intake opening in fluid communication with said openings formed by collar element 33 and a vapor outlet opening in fluid communication with a suitable analytic system, such as a chromatographic analysis system, is disposed upstream of collar element 33. Mobility of drill bit assembly 10 is provided by means of an adjustable column 16 and a rotational motor system 14.

In accordance with one embodiment of this invention, a chromatographic analysis system 15 is operably coupled to the upstream end 22 of drill bit assembly 10 and in fluid communication with the vapor outlet opening of vapor conduit 12. In accordance with one particularly preferred embodiment of this invention, chromatographic analysis system 15 is operably coupled to drill bit assembly 10 proximate to drill bit assembly 10, such that as drill bit assembly 10 progresses during operation of the drilling apparatus, the chromatographic analysis system 15 remains in close proximity to drill bit assembly 15. In this embodiment, chromatographic analysis system 15 comprises signal transmission means suitable for communicating data generated by the chromatographic analysis system up to the earth's surface for processing. In accordance with one embodiment, the signal transmission means comprises at least one optical fiber 34 extending between chromatographic analysis system 15 and a data receiver disposed above ground (not shown).

In accordance with an alternative embodiment of this invention, chromatographic analysis system 15 is operably connected to drill bit assembly 10 albeit distal from drill bit assembly 10. Typically, in accordance with this embodiment, the chromatographic analysis system 15 is disposed above ground and vapor conduits 12 extend from drill bit assembly 10 to the surface for transmission of the collected vapors to the chromatographic analysis system 15. To prevent condensation of the vapor during transmission to the surface, which condensation would prevent chromatographic analysis and potentially damage the equipment comprising the chromatographic analysis system, it is necessary that the temperature and pressure associated with vapor conduits 12 be maintained accordingly. In accordance with one embodiment of this invention, means are provided for maintaining the temperature and pressure of the vapors transmitted through vapor conduits 12. When the vapors are successfully captured at the surface, they can be analyzed to determine the characteristics of the rock formation being drilled.

In accordance with one embodiment of this invention, a laser spectroscopy assembly 17 oriented to transmit one or more laser beams in the direction of the wellbore wall is operably connected to drill bit assembly 10. By analyzing the reflections of the laser beam incident to the wellbore wall surface, properties of the materials forming the wellbore wall, typically rock, can be determined. To prevent dust from interfering with the transmission of these laser beams, drill bit assembly 10 further comprises a plurality of purging nozzles 39 through which a purging gas is transmitted, thereby precluding the build-up of potentially interfering dust in the area surrounding laser spectroscopy assembly 17. Because the objective of this laser is to analyze reflections rather than destroy the rock, compared to the laser employed in the laser cutting system for drilling, a relatively low power laser should be used. By way of example, a HeNe laser would be suitable for use in connection with this application. The laser is emitted in one or more beams from the laser spectroscopy assembly 17 through openings 24 thereof into an area adjacent to the direct drilling location. Lenses 38 are provided to capture the reflection of this laser light from the rock surface. The data thus collected can either be analyzed by a down-hole processing device or delivered to the surface for analysis. If laser spectroscopy is employed independent of chromatographic analysis, conventional drill bits rather than laser drill bits may be utilized. In this case, an independent laser spectroscopy apparatus may be used to analyze rock formations during conventional drilling. That is, the apparatus may be lowered down hole and used independently of the drill bit.

It will be apparent to those skilled in the art that one of the benefits of this invention is the large amount of information that can be provided about the rock formations at a higher data rate than conventional systems. The time required to transport the vapor back to the surface by way of vapor conduits 20 as well as the time required to transmit light data by means of optical fibers is considerably shorter than the time required to transport physical shards of rock through drilling fluid in accordance with conventional methods.

While in the foregoing specification this invention has been described in relation to certain preferred embodiments thereof, and many details have been set forth for purposes of illustration, it will be apparent to those skilled in the art that the apparatus is susceptible to additional embodiments and that certain of the details described herein can be varied considerably without departing from the basic principles of the invention.

We claim:

1. A drilling apparatus for well-boring comprising:
    a drill bit assembly comprising a laser cutting assembly, a vacuum assembly adapted to intake vapors generated by said laser cutting assembly proximate said drill bit assembly during operation of said drilling apparatus, and at least one of a laser spectroscopy assembly and a chromatographic analysis system adapted to determine at least one property of rock encountered during operation of said drilling apparatus.

2. A drilling apparatus in accordance with claim 1 further comprising at least one data transmission conduit connected to said at least one of said laser spectroscopy assembly and said chromatographic analysis system and adapted to transmit data from said at least one of said laser spectroscopy assembly and said chromatographic analysis system to an above-ground data receiver.

3. A drilling apparatus in accordance with claim 1 further comprising at least one mechanical cutting element operably connected to said drill bit assembly downstream of said laser cutting assembly, said at least one mechanical cutting element forming at least one through opening whereby a laser beam generated by said laser cutting assembly is transmitted from said laser cutting assembly to an area downstream of said drill bit assembly.

4. A method for drilling a well comprising the steps of:
    positioning a drill bit assembly comprising a laser cutting assembly oriented to transmit at least one laser beam into a weilbore in said wellbore;
    transmitting said at least one laser beam ahead of said drill bit assembly, whereby material ahead of said drill bit assembly is at least one of volatilized, softened and melted;
    capturing at least a portion of vapors proximate said drill bit assembly resulting from said transmission of said at least one laser beam, creating captured vapors;
    transferring said captured vapors to a chromatographic analysis system disposed in said wellbore proximate said drill bit assembly;
    analyzing said captured vapors using said chromatographic analysis system; and
    adjusting said drilling of said well based upon results obtained from said analysis.

5. A method in accordance with claim 4, wherein said results are communicated to a data receiver disposed above ground.

6. A method in accordance with claim 4 further comprising transmitting at least one additional laser beam in a direction of a weilbore wall surface and analyzing reflections of said additional laser beam off said welibore wall surface, whereby at least one property of material forming said weilbore wall is determined.

7. A method in accordance with claim 4 further comprising drilling said weilbore using at least one mechanical cutting element.

8. A method in accordance with claim 4, wherein said laser cutting assembly comprises a laser source integral with said drill bit assembly.

9. A method in accordance with claim 4, wherein said laser cutting assembly comprises at least one optical fiber operably connected to a laser source disposed above said ground.

* * * * *